(12) United States Patent
Zach

(10) Patent No.: US 9,472,920 B2
(45) Date of Patent: Oct. 18, 2016

(54) GENERATING TWO SYNCHRONIZED TRAINS OF LASER PULSES

(71) Applicant: Toptica Photonics AG, Graefelfing (DE)

(72) Inventor: Armin Zach, Windach (DE)

(73) Assignee: Toptica Photonics AG, Graefelfing (DE)

( * ) Notice: Subject to any disclaimer, the term of this patent is extended or adjusted under 35 U.S.C. 154(b) by 0 days.

(21) Appl. No.: 14/624,776

(22) Filed: Feb. 18, 2015

(65) Prior Publication Data

US 2016/0240994 A1   Aug. 18, 2016

(51) Int. Cl.
*H01S 3/094* (2006.01)
*H01S 3/067* (2006.01)
*H01S 3/109* (2006.01)
*H01S 3/10* (2006.01)
*H01S 3/16* (2006.01)
*H01S 3/11* (2006.01)

(52) U.S. Cl.
CPC ......... *H01S 3/094076* (2013.01); *H01S 3/067* (2013.01); *H01S 3/06708* (2013.01); *H01S 3/094003* (2013.01); *H01S 3/10007* (2013.01); *H01S 3/109* (2013.01); *H01S 3/10023* (2013.01); *H01S 3/1118* (2013.01); *H01S 3/163* (2013.01); *H01S 3/1611* (2013.01); *H01S 3/1613* (2013.01); *H01S 3/1618* (2013.01)

(58) Field of Classification Search
CPC .. H01S 3/108; H01S 3/094076; H01S 3/067; H01S 3/06708; H01S 3/094003; H01S 3/10007; H01S 3/10023; H01S 3/109; H01S 3/1118
See application file for complete search history.

(56) References Cited

PUBLICATIONS

P. Gross et al., Single-laser light source for CARS microscopy based on soliton self-frequency shift in a microstructured fiber, Applied Physics B, 2010, vol. 101, pp. 167-172.

*Primary Examiner* — Armando Rodriguez
(74) *Attorney, Agent, or Firm* — Collard & Roe, P.C.

(57) ABSTRACT

A method and system generates two synchronized trains of laser pulses at different wavelengths, wherein the two pulse trains are temporally synchronized and have a stable phase relation, and wherein the wavelength of one of the pulse trains is de-tunable. The method includes the steps of: generating a train of ultra-short seed laser pulses; splitting the train of seed laser pulses into a first pulse train and a second pulse train; and frequency-shifting the first pulse train by soliton self-frequency shift in an optically pumped waveguide having anomalous dispersion, wherein the spectrum of the frequency-shifted first pulse train is de-tunable by varying the pump power.

21 Claims, 2 Drawing Sheets

GENERATING TWO SYNCHRONIZED TRAINS OF LASER PULSES

FIELD OF THE INVENTION

The invention relates to a method and to a system for generating two synchronized beams of laser pulses.

BACKGROUND OF THE INVENTION

The invention generally relates to light sources for generating two high-intensity trains of laser pulses at different wavelengths, wherein the two pulse trains are temporally synchronized and have a stable phase relation.

Such light sources are applied, for example, in coherent anti-Stokes Raman scattering (CARS) microscopy. CARS is a nonlinear imaging technique that offers chemical selectivity and three-dimensional resolution. In order to obtain a CARS signal, two light waves with different frequencies are spatially and temporally overlapped in a sample. Then, a vibrational level at the frequency corresponding to the difference of the frequencies of the two light waves is excited. This results in a molecule-specific response and thus provides chemically selective contrast. Tightly focusing the two light waves in a scanning microscope, the CARS signal is generated exclusively in the focus volume, which enables high three-dimensional spatial resolution.

P. Groβ et al (Appl. Phys. B, 2010, vol. 101, pp. 167-172) describe a laser light source, which is based on a single Titanium-Sapphire femtosecond laser oscillator. A second wavelength is derived from the primary laser by soliton self-frequency shift in a micro-structured optical fiber (MSF) and subsequent amplification. The second wavelength is de-tuned by varying the output power of the Titanium-Sapphire laser as the soliton dynamics within the MSF depend on the power of the radiation propagating in the MSF.

SUMMARY OF THE INVENTION

It is an object of the invention to provide an improved and universally applicable method and system for generating two trains of laser pulses at different wavelengths, wherein the two pulse trains are temporally synchronized and have a stable phase relation, and wherein the wavelength of one of the pulse trains is de-tunable.

In accordance with the invention, a method for generating two synchronized trains of laser pulses is disclosed, which method comprises the steps of:
 generating a train of ultra-short seed laser pulses,
 splitting the train of seed laser pulses into a first pulse train and a second pulse train;
 frequency-shifting the first pulse train by soliton self-frequency shift in an optically pumped waveguide having anomalous dispersion, wherein the spectrum of the frequency-shifted first pulse train is de-tuned by varying the pump power.

According to the invention, ultra-short seed laser pulses having a pulse duration of less than 1 ps are generated by a single seed laser source, which may be, for example, a passively SESAM mode-locked all-fiber laser oscillator. The train of seed laser pulses is split into a first pulse train and a second pulse train. The pulse trains are synchronized and have a perfectly stable phase relation as both pulse trains are derived from the same seed laser source. It is the gist of the invention to achieve variable frequency-shifting of the first pulse train by soliton self-frequency shift in an optically pumped waveguide having anomalous dispersion. The spectrum of the frequency-shifted first pulse train can be de-tuned simply by varying the pump power of the optical pumping of the waveguide.

The method of the invention can be implemented effectively in an all-fiber setup adopting the per se known master-oscillator power amplifier (MOPA) concept, wherein the first and/or second pulse trains are amplified for obtaining the required power levels. Utilizing the effects of soliton self-compression and soliton self-frequency shift enables an all-fiber approach with no need for bulk compression optics.

The optical waveguide operating as a soliton amplifier according to the invention requires anomalous dispersion. It is known that solitons in optical waveguides can transfer energy from higher to lower frequency components due to the effect of intra-pulse stimulated Raman scattering. For solitons with pulse durations of less than 100 fs the optical spectrum broadens to such an extent that the longer wavelength tail experiences Raman amplification at the expense of power at shorter wavelengths. This leads to an overall spectral shift of the soliton towards longer wavelengths. This effect is referred to herein as soliton self-frequency shift. The extent of the soliton self-frequency shift depends on the propagation length of the laser pulses within the wave guide and on the pump power. This is exploited according to the invention for de-tuning the spectrum of the first pulse train by varying the pump power of the optically pumped wave guide. The variation of the pump power leaves the soliton energy unaffected. The pulses of the frequency-shifted first pulse train are bandwidth-limited, have a very 'clean' pulse shape and no chirp.

However, the energy of the Raman shifted soliton is limited due to the effective area of the so far available actively doped fibers. In order to achieve an increased energy level a larger effective area is required. According to preferred embodiments of the invention, new fiber technologies like very large mode area (VLMA) fibers and higher order mode (HOM) fibers are used as optical waveguides without compromising the spatial beam quality.

In one possible embodiment, the optically pumped waveguide is a rare-earth-doped VLMA fiber having an effective area of at least 500 $\mu m^2$, preferably at least 1000 $\mu m^2$. With such a fiber, a soliton energy of more than 10 nJ at a repetition rate of about 100 MHz can be achieved.

In an alternative embodiment, the optically pumped waveguide is a rare-earth-doped HOM optical fiber having an effective area of at least 2000 $\mu m^2$, preferably at least 5000 $\mu m^2$. With such a waveguide, a soliton energy of more than 100 nJ at a repetition rate of about 100 MHz is achievable.

In yet another embodiment, the optically pumped waveguide is a rare-earth-doped rod-type optical fiber having an effective area of at least 2000 $\mu m^2$, preferably at least 5000 $\mu m^2$. Rod-type optical fibers having an effective mode area of up to 10000 $\mu m^2$ are available. With such a waveguide, a soliton energy of more than 250 nJ at a repetition rate of about 100 MHz is achievable. However, these fibers are not bendable which restricts their application in practice.

According to still another embodiment, the optically pumped waveguide is a rare-earth-doped micro structured optical fiber, like, for example, a photonic crystal fiber (PCF) or a photonic bandgap fiber (PBG) with either a hollow core or a solid core, having an effective area of at least 500 $\mu m^2$, preferably at least 5000 $\mu m^2$.

The fibers may be rare earth doped, preferably with $Er^{3+}$, $Tm^{3+}$ or $Yb^{3+}$ ions, or even co-doped, e.g. $Er^{3+}/Yb^{3+}$.

In a preferred embodiment of the invention, the frequency-shifted first pulse train and the second pulse train are superposed in a nonlinear optical medium for generating a third pulse train by frequency-mixing the first and second pulse trains. In this way, it is possible to obtain light pulses in different frequency regions. For example, laser pulses in the mid/long-wavelength infrared spectral range between 5 and 15 μm may be generated by difference frequency generation from a first pulse train tunable between 1.6 μm and 2.0 μm and a second pulse train at 1.55 μm.

In another preferred embodiment of the invention, the frequency-shifted first pulse train is frequency-doubled by using an appropriate non-linear optical medium. In order to meet the phase-matching condition for the de-tunable first pulse train, a periodically poled Lithium Niobate crystal (PPLN) may be employed in practice. This allows, for example, to obtain a tunable wavelength of the frequency shifted and frequency-doubled first pulse train around 800 nm, wherein the wavelength of the second pulse train is in the range from 900-1200 nm. These wavelength ranges render the technique of the invention particularly interesting for providing a laser light source for coherent anti-Stokes Raman scattering (CARS) microscopy (see above).

The invention not only relates to a method but also to a system for generating two synchronized trains of laser pulses, which system comprises:
- a seed laser source which generates a train of ultra-short seed laser pulses;
- a splitting means which splits the train of seed laser pulses into a first pulse train and a second pulse train;
- an optically pumped waveguide through which the first pulse train propagates, wherein the optically pumped waveguide has anomalous dispersion and wherein the spectrum of the frequency-shifted first pulse train is de-tunable by varying the pump power.

The seed laser source of the system may be, for example, an all-fiber passively mode-locked oscillator (for example Erbium-based) which is followed by a fiber-based beam splitter for splitting the train of seed laser pulses into a first pulse train and a second pulse train. The first and second pulse trains may be amplified in appropriate fiber amplifiers (for example $Er^{3+}$-doped pumped optical fibers). The first pulse train is propagated through a (rare-earth-doped) optically pumped waveguide in which the first pulse train experiences soliton self-frequency shift. As mentioned above, the optical waveguide is preferably a rare earth doped VLMA or a rare earth doped HOM fiber in order to obtain a high as possible soliton energy. The soliton self-frequency shift can be controlled by varying the pump power, wherein the variation of the pump power leaves the soliton energy constant.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
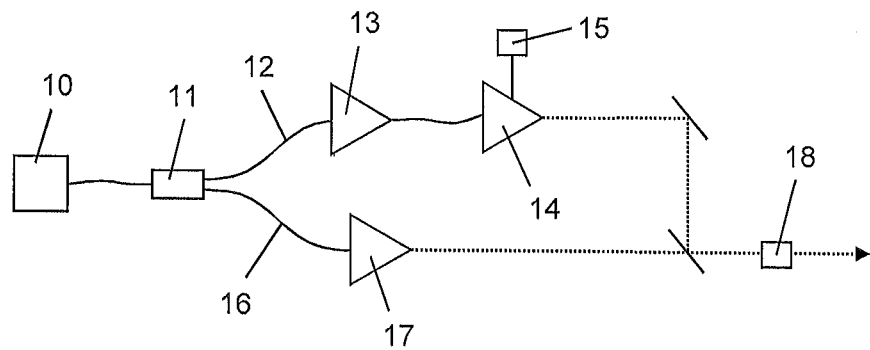
FIG. 1 schematically shows a first embodiment of a laser system according to the invention.

FIG. 1 schematically shows a first embodiment of a laser system according to the invention. The system comprises a seed laser source 10 generating a train of ultra-short seed laser pulses at 1.56 μm having a pulse duration of about 100 fs (FWHM) and a repetition frequency of about 100 MHz. The seed laser source 10 may be, for example, a passively mode-locked all fiber Erbium-based oscillator of well-known, commercially available type. The output laser pulses of the seed laser source 10 are split by a fiber beam splitter 11.

Figure 3:
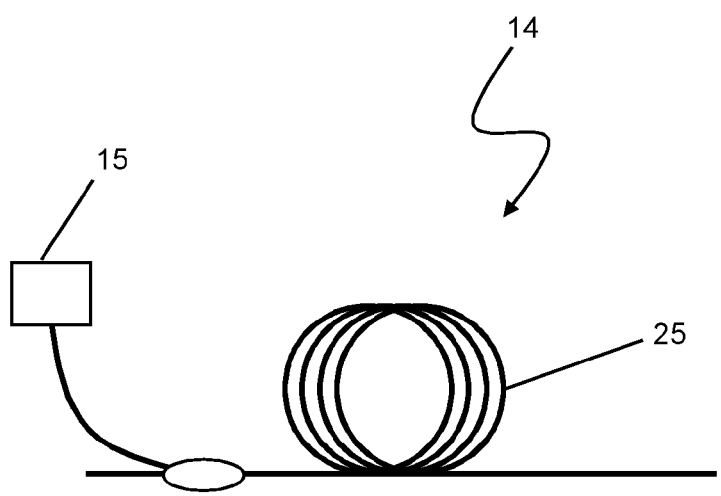
FIG. 3 schematically shows an optically pumped waveguide used as an amplifier in the laser system of FIG. 1 or FIG. 2.

A first pulse train is delivered via fiber section 12 to an $Er^{3+}$-doped fiber pre-amplifier 13 with normal dispersion. The amplified first pulse train is coupled into an amplifier 14 (see FIG. 3) comprising about 2-3 m of optically Pumped $Er^{3+}$-doped VLMA fiber 25 having an effective area of about 1000 μm². The VLMA fiber 25 has anomalous dispersion. The laser pulses of the first pulse train experience soliton compression amplification in the VLMA fiber 25 up to a certain limit, which is defined by the soliton energy. As soon as this limit is exceeded a second soliton splits off and experiences soliton self-frequency shift towards longer wavelength. The VLMA fiber 25 is core-pumped by a pump laser 15, preferably a Raman pump laser at 1460 nm. The pre-amplified laser pulses of the first pulse train injected into the VLMA fiber 25 have a pulse duration of about 400 fs (FWHM) with an average power of about 90 mW. By varying the pump power of the pump laser 15 between 3 W and about 50 W the soliton self shifted part of the spectrum of the first pulse train can be de-tuned from 1.58 μm to about 2 μm while keeping the pulse energy stable around 15 nJ with a pulse duration of about 110 fs. With proper coiling of the VLMA fiber 25 a nearly perfect Gaussian beam profile can be achieved.

A second pulse train is delivered via fiber section 16 to an amplifier 17 comprising an $Er^{3+}$-doped nonlinear fiber amplifier as well as a section of compression fiber (not depicted). The output beams of the soliton amplifier 14 and the amplifier 17 are superposed in a nonlinear optical medium 18 in which a third pulse train is generated by difference frequency generation. The wavelength of the laser pulses of the third pulse train at the output of the depicted system is de-tunable in the mid/long-infrared range from 5 μm to 15 μm by varying the power of the pump laser 15.

Figure 2:
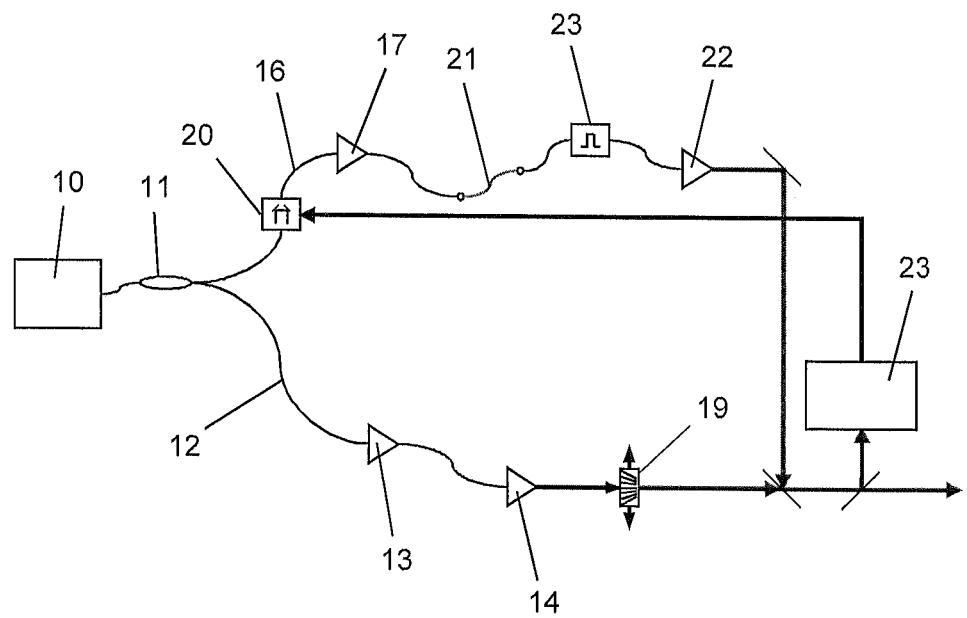
FIG. 2 schematically shows a second embodiment of a laser system according to the invention.

FIG. 2 shows a system according to the invention for application in CARS microscopy. The system comprises a seed laser source 10 and a fiber beam splitter 11 as described before with reference to FIG. 1.

The amplified and soliton self frequency-shifted first pulse train is frequency-doubled in a periodically poled Lithium Niobate crystal with a fan-out structured poling period 19 which can be variably phase matched by moving it in a direction perpendicular to the output beam of the soliton self frequency shifting amplifier 14 (as indicated by the arrows). The thickness of the crystal 19 determines the spectral bandwidth and thus the pulse duration of the frequency-double laser pulses. With a thickness of the crystal 19 of about 10 mm, the duration of the frequency-doubled laser pulses of the first pulse train is about 1 ps. With a thickness of the crystal 19 of about 0.5 mm, the duration of the frequency-doubled laser pulses of the first pulse train is about 100 fs.

The second pulse train passes a delay line 20 before it is delivered to nonlinear $Er^{3+}$-doped fiber amplifier 17. The amplified laser pulses of the second pulse train are frequency-shifted in a section of highly nonlinear optical fiber 21 into the 1 µm spectral region. An up-stream spectral filter 23 has a narrow pass band of about 1.5 nm spectral width. The frequency-shifted and spectrally filtered laser pulses are then further amplified by an $Yb^3$-doped fiber amplifier 22. The laser pulses of the second pulse train at the output of amplifier 22 are bandwidth-limited and have an average power of about 500 mW and a pulse duration of 0.5-1.0 ps.

In the depicted embodiment, the wavelength of the frequency shifted and frequency-doubled first pulse train is thus tunable around 800 nm by varying the pump power of the soliton amplifier 14 while the spectrum of the second pulse train is in the 1 µm spectral region. The first and second pulse trains are superposed and delivered to a CARS microscopy system to be focused into a sample.

An interesting spectral window in CARS microscopy starts at 2.800 $cm^{-1}$ and reaches up to 3.400 $cm^{-1}$. It is used to detect aliphatic and aromatic C—H stretching vibrational bands, lipids, proteins and water. To generate this spectral bandwidth, a tunability from 780 nm up to 820 nm for the pump wavelength and 1060 nm for the Stokes wavelength is needed.

Further provision is made in the depicted embodiment for a timing control circuit 24 which detects the phase difference of the first and second pulse trains and controls the delay line 20 in order to obtain temporal coincidence of the laser pulses of the first and second pulse trains at the output of the system.

Instead the VLMA fiber 25, a rare-earth-doped higher order mode fiber, a rare-earth-doped rod-type fiber, or a rare-earth-doped micro structured fiber may be used.

What is claimed is:

1. Method for generating two synchronized trains of laser pulses, comprising the steps of:
   generating a train of ultra-short seed laser pulses,
   splitting the train of seed laser pulses into a first pulse train and a second pulse train;
   frequency-shifting the first pulse train by soliton self-frequency shift in an optically pumped waveguide having anomalous dispersion, wherein the spectrum of the frequency-shifted first pulse train is de-tunable by varying the pump power.

2. Method of claim 1, wherein the optically pumped waveguide is a rare-earth-doped large mode area fiber having an effective area of at least 500 $\mu m^2$.

3. Method of claim 1, wherein the optically pumped waveguide is a rare-earth-doped higher order mode fiber having an effective area of at least 2000 $\mu m^2$.

4. Method of claim 1, wherein the optically pumped waveguide is a rare-earth-doped rod-type fiber having an effective area of at least 2000 $\mu m^2$.

5. Method of claim 1, wherein the optically pumped waveguide is a rare-earth-doped micro structured optical fiber having an effective area of at least 500 $\mu m^2$.

6. Method of claim 1, further comprising the step of amplifying at least one of the first pulse train and the second pulse train.

7. Method of claim 1, further comprising the step of superposing the frequency-shifted first Pulse train and the second pulse train in a nonlinear optical medium and generating a third pulse train by frequency-mixing the first and second pulse trains.

8. Method of claim 1, further comprising the step of frequency-doubling the frequency-shifted first pulse train.

9. Method of claim 8, wherein the wavelength of the frequency shifted and frequency-doubled first pulse train is tunable around 800 nm, by varying the pump power, wherein the wavelength of the second pulse train is in the range from 900-1300 nm.

10. System for generating two synchronized trains of laser pulses, comprising:
    a seed laser source which generates a train of ultra-short seed laser pulses;
    a splitter which splits the train of seed laser pulses into a first pulse train and a second pulse train;
    an optically pumped waveguide through Which the first pulse train propagates, wherein the optically pumped waveguide has anomalous dispersion, wherein the first pulse train is frequency-shifted, and wherein the first pulse train so frequency-shifted has a spectrum de-tunable by varying the pump power.

11. System of claim 10, wherein the optically pumped waveguide is a rare-earth-doped large mode area fiber having an effective area of at least 500 $\mu m^2$.

12. System of claim 10, wherein the optically pumped waveguide is a rare-earth-doped higher order mode fiber having an effective area of at least 2000 $\mu m^2$.

13. System of claim 10, wherein the optically pumped waveguide is a rare-earth-doped rod-type fiber having an effective area of at least 2000 $\mu m^2$.

14. System of claim 10, wherein the optically pumped waveguide is a rare-earth-doped micro structured optical fiber having an effective area of at least 500 $m^2$.

15. System of claim 10, further comprising at least one optical amplifier which amplifies at least one of the first pulse train and the second pulse train.

16. System of claim 10, further comprising a nonlinear optical medium in which the first pulse train so frequency-shifted, and the second pulse train are superposed.

17. System of claim 10, further comprising a periodically poled Lithium Niobate crystal which frequency-doubles the first pulse train so frequency-shifted.

18. System of claim 10, wherein the seed laser source comprises a passively SESAM mode-locked fiber oscillator.

19. System of claim 10, wherein the seed laser pulses of the second pulse train are frequency-shifted in a highly nonlinear fiber into the spectral region of 900-1300 nm.

20. System of claim 19, wherein the second pulse train so frequency-shifted is amplified in a rare earth-doped optical fiber.

21. System of claim 20, wherein the frequency-shifted and amplified pulse train is spectrally filtered to obtain bandwidth-limited pulses, with a pulse duration of 0.2 to 5 ps.

* * * * *